(12) United States Patent
Boesser et al.

(10) Patent No.: US 8,154,595 B2
(45) Date of Patent: Apr. 10, 2012

(54) DEVICE AND METHOD FOR AUTOMATIC DETECTION OF INCORRECT MEASUREMENTS BY MEANS OF QUALITY FACTORS

(75) Inventors: Hans-Artur Boesser, Breidenbach (DE); Michael Heiden, Wolfersheim (DE); Klaus-Dieter Adam, Jena (DE)

(73) Assignee: Vistec Semiconductor Systems Jena GmbH, Jena (DE)

( * ) Notice: Subject to any disclaimer, the term of this patent is extended or adjusted under 35 U.S.C. 154(b) by 1106 days.

(21) Appl. No.: 12/023,222

(22) Filed: Jan. 31, 2008

(65) Prior Publication Data

US 2008/0202201 A1    Aug. 28, 2008

Related U.S. Application Data

(60) Provisional application No. 60/891,333, filed on Feb. 23, 2007.

(30) Foreign Application Priority Data

Feb. 23, 2007  (DE) .................. 10 2007 009 446
Dec. 12, 2007  (DE) .................. 10 2007 047 924

(51) Int. Cl.
*H04N 7/18*     (2006.01)
*G06K 9/00*     (2006.01)
*G01B 11/14*    (2006.01)

(52) U.S. Cl. ................. 348/135; 382/145; 356/614

(58) Field of Classification Search .......... None
See application file for complete search history.

(56) References Cited

U.S. PATENT DOCUMENTS

| 5,512,842 | A | 4/1996 | Kida |
| 6,323,953 | B1 * | 11/2001 | Blaesing-Bangert et al. 356/614 |
| 6,610,550 | B1 * | 8/2003 | Pasadyn et al. ............... 438/14 |

(Continued)

FOREIGN PATENT DOCUMENTS

EP     0628806 A2    12/1994

(Continued)

OTHER PUBLICATIONS

Blasing, C., "Pattern Placement Metrology for Mask Making," SEMI, Mar. 31, 1998.

(Continued)

*Primary Examiner* — Wen-Tai Lin
(74) *Attorney, Agent, or Firm* — Houston Eliseeva, LLP (57) ABSTRACT

What is disclosed is a device (1) for automatic detection of a possible incorrect measurement, wherein the device (1) comprises at least one reflected light illumination apparatus (14) and/or a transmitted light illumination apparatus (6) and at least one imaging optical system (9) and one detector (11) of a camera (10) for imaging structures (3) on a substrate (2), wherein a first program portion (17) is linked to the detector (11) of the camera (10), said detector being provided for determining the position and/or dimension of the structure (3) on the substrate (2), wherein the device (1) determines and records a plurality of measurement variables $M_j$, $j \in \{1, \ldots, L\}$, from which at least one variable G can be determined, wherein a second program portion (18) is linked to the detector (11) of the camera (10), said program portion calculating an analysis of the measurement variables $M_j$ with regard to a possible incorrect measurement. Also disclosed is a method for automatic detection of a possible incorrect measurement wherein an analysis of the measurement variables $M_j$ with regard to a possible incorrect measurement is calculated with a second program portion (18) which is linked to the detector (11) of the camera (10).

21 Claims, 5 Drawing Sheets

U.S. PATENT DOCUMENTS

| | | |
|---|---|---|
| 6,920,249 B2 | 7/2005 | Rinn et al. |
| 6,980,304 B2 | 12/2005 | Broermann et al. |
| 7,242,484 B2 * | 7/2007 | Shirley .......................... 356/604 |
| 7,533,313 B1 * | 5/2009 | Retersdorf et al. ............ 714/724 |
| 2004/0179190 A1 * | 9/2004 | Miyashita et al. ............ 356/124 |
| 2006/0206851 A1 | 9/2006 | Van Wingerden et al. |
| 2006/0269117 A1 | 11/2006 | Seitz et al. |

FOREIGN PATENT DOCUMENTS

| | | |
|---|---|---|
| JP | 2004259909 A | 9/2004 |
| WO | 00/60415 A1 | 10/2000 |
| WO | 2006/089630 A1 | 8/2006 |

OTHER PUBLICATIONS

Mirande, W., "Edge Measurement on Microstructures," VDI Berichte Nr. 1102 (1993), pp. 137-159.

Schlueter, G. et al., "Next generation mask metrology tool," Proc. of SPIE vol. 4754, 758-768 (2002).

* cited by examiner

DEVICE AND METHOD FOR AUTOMATIC DETECTION OF INCORRECT MEASUREMENTS BY MEANS OF QUALITY FACTORS

RELATED APPLICATIONS

This application claims priority to German Patent Application No. 10 2007 009 446.0, filed on Feb. 23, 2007, and German Patent Application No. 10 2007 047 924.9, filed on Dec. 12, 2007, and claims the benefit under 35 USC 119(e) of U.S. Provisional Application No. 60/891,333 filed on Feb. 23, 2007, all of which are incorporated herein by reference in their entirety.

BACKGROUND OF THE INVENTION

The invention relates to a device for automatic detection of a possible incorrect measurement. In particular, the invention relates to the automatic detection of a possible incorrect measurement in a coordinate measuring machine, wherein the device comprises at least one reflected light illumination apparatus and/or a transmitted light illumination apparatus and at least one imaging optical system and one detector of a camera for imaging structures on a mask (substrate), wherein a first program portion is linked to the detector of the camera, said detector being provided for determining the position and/or dimension of the structure on the mask, wherein the device determines and records a plurality of measurement variables $M_j$, $j \in \{1, \ldots, L\}$, from which at least one variable G can be determined. G can be the position or the structural width (CD, critical dimension) of the structure on the mask.

The invention also relates to a method for automatic detection of a possible incorrect measurement. In particular, the invention relates to a method for automatic detection of a possible incorrect measurement in a coordinate measuring machine, wherein at least one structure on the mask for semiconductor production is illuminated with at least one reflected light illumination apparatus and/or one transmitted light illumination apparatus, the structure on the mask is imaged by at least one imaging optical system on a detector of a camera, during measurement of the structure on the mask in relation to the position and/or dimension the values are determined by means of a first program portion that is linked to the detector of the camera, and wherein a plurality of measurement variables $M_j$, $j \in \{1, \ldots, L\}$, is determined and recorded, wherefrom at least one variable G is determined.

It is fundamentally impossible to make measurements without errors. Due to various causes, the variable G to be measured is not correctly detected. An incorrect measurement (measurement deviation) is understood to mean a measurement value that has a greater deviation from the true value of the variable G to be measured than is the case according to the statistical average. A position measurement can be disrupted, for example, by the sudden opening of a door or by floor vibration and thereby lead to incorrect measurements. A number of other parameters influence the measured position or CD of a structure on the substrate. These parameters may be, for example, pressure, temperature, the tilt angle or profile shape of the structure on the substrate, deviations in the intensity of the measured profile, etc. Apart from the microscope with a camera as described below, at least one laser distance measuring system (X-Y etalon axis) is needed.

The measurement of structures on a substrate, such as a mask, is carried out with a coordinate measuring machine. A coordinate measuring machine of this type is sufficiently well known from the prior art. Reference is made in this regard, for example, to the lecture manuscript "Pattern Placement Metrology for Mask Making" by Dr. Carola Bläsing. The lecture was given at the Semicon Education Programme congress in Geneva on 31 Mar. 1998, and describes the coordinate measuring machine in detail.

Since the present invention can be advantageously used in a measuring device of this type, the embodiments of the present invention on the following pages are described—without restricting its scope—primarily in relation to a measuring device of this type. In the context of the present invention, the terms "sample", "substrate", "mask" and the general expression "object" are taken to have equivalent meanings. The coordinate measuring machine is placed in a climate chamber in order to be able to achieve measuring accuracy in the nanometer range. What is measured is the coordinates of structures on masks and wafers. The measuring system is arranged on a block mounted in vibration damping manner. The block is preferably constructed as a granite block. The masks and wafers are mounted on a measuring table with an automatic handling system. In the production of semiconductor chips arranged on wafers, with increasing component density, the width of the individual structures becomes ever smaller. Therefore the demands placed on the specifications of coordinate measuring machines used as measuring and inspection systems for measuring the edges and the positions of the structures and for measuring the CD also increase. As previously, optical sensing methods in conjunction with laser displacement measuring systems are still favoured for these machines although the required measuring accuracy (currently in the range of a few nanometers) lies far below the resolving power achievable with the light wavelength used (light with a wavelength of less than or equal to 400 nm). The advantage of optical measuring equipment lies in the substantially less complex construction as well as its simplicity in use compared with systems using other sensing methods or with X-ray or electron beams.

The construction of a coordinate measuring machine of this type, as known, for example, from the prior art will now be described in greater detail by reference to FIG. 1. A method and a measuring device for determination of the position of structures on a substrate are known from the unexamined German published application DE 10047211 A1. Therefore with regard to details of the position determination as described, reference should be expressly made to this document. However, the coordinate measuring machine is not suitable for calculating an analysis of specified measurement variables $M_j$ with regard to a possible incorrect measurement.

The German patent application DE 19819492 describes a measuring machine for structural widths or the position of structures on the substrate. Herein, the measuring table slides on air bearings on the surface of the granite block. Mounted on two mutually perpendicular sides of the measuring table are planar mirrors. A laser interferometer system determines the position of the measuring table. Some other clean room-compatible guidance of the measuring table is also conceivable. The illumination and the imaging of the structures to be measured is carried out with a high-resolution apochromatically corrected microscope lens and with reflected light or transmitted light in the spectral range of the near UV or light having a wavelength of less than or equal to 400 nm. CCD camera serves as the detector. Measurement signals are obtained from the pixels of the detector array that lie within a measuring window. From this, an intensity profile of the measured structure is derived by means of image processing, from which, for example, the edge position of the structure is determined.

The measured edge position depends on the physical quality of the edge itself, on the optical measuring method used, and also on the quality of the imaging system. The correlation is described in the document "Edge Measurement on Microstructures", by W. Mirandé, VDI Reports No. 1102 (1993), pages 137 ff. If the position of the structure is defined by the midline between the two edges, in general, the factors influencing the measured edge position have no effect on the measured position of the structure. However, evaluation of the measurement results for a measurement of structure width can lead to different results in different measuring devices.

During semiconductor production, the mask is illuminated in the stepper using transmitted light illumination and imaged on the wafer. It is therefore of interest to be able to determine the precise light-shading width of the structural element. Special measuring microscopes with which the mask is illuminated using transmitted light and only the width of the opaque structure is measured have been developed for this purpose. These measuring devices are not provided for determining the position coordinates of the structural elements. These considerations apply in the same way if, in place of opaque structural elements, transparent structural elements in the mask surface are to be measured.

The German patent application DE 10 2005 009 536 A1 describes a method for mask inspection which can be used within the context of mask design during mask production, in order to identify relevant weak-spots and correct them at an early stage. It is thus intended that errors should be identified in the mask layout and the mask design so that the masks that are produced have a smaller error quota and therefore costs are minimised.

The AIMS<TM> (Aerial Imaging Measurement System) from Carl Zeiss SMS GmbH has been established on the market for 10 years for the analysis of mask defects with regard to printability. Herein a small region of the mask (the defect site with its surroundings) is illuminated and imaged using the same illumination and imaging conditions (wavelength, NA (numerical aperture), illumination type, coherence level of the light (Sigma)) as in a lithographic scanner. In contrast to a scanner, however, the aerial image that is formed of the mask is enlarged onto a CCD camera. The camera sees the same latent image as the photoresist on the wafer. Therefore the aerial image can be analysed without complex test prints using wafer exposure devices and conclusions can be drawn about the printability of the mask. By recording a focus series, additional information is gathered regarding the analysis of the lithographic processing window (in this regard, see DE10332059 A1).

The German patent application DE 10332059 A1 describes a method for analysing objects in microlithography, preferably on masks, by means of an Aerial Image Measurement System (AIMS), which comprises at least two imaging stages, wherein the detected image is corrected with regard to transmission behaviour by means of a correction filter of the second or further imaging stages and the illumination of the object is carried out using reflected and/or transmitted light illumination, wherein the correction is carried out in a manner such that the corrected starting variables correspond to those of an image from a photolithography stepper or scanner, wherein the correction takes place by folding back and measured or calculated correction values are used for the correction.

The European patent application EP 0 628 806 describes a device and a method for determining the characteristics of a photolithographic mask. In the AIMS mask inspection microscope, for example, the setting and observation of certain illumination settings is linked thereto. The illumination light in this case comes from the UV region. The detector or the image recording unit is a UV CCD camera.

The international patent application WO 00/60415 A1 describes a method for correcting imaging errors, wherein by modifying an electronic mask design, following illumination of this mask design, structures that approach the original mask design or the intended mask as closely as possible are imaged on the mask with a mask writer. The process conditions that need to be taken into account are summarised in the form of tables containing, in particular, the parameters which depend on the process conditions, given in the form of correction values. For example, the tables include site-dependent correction values for compensation of the device-specific aberration of the mask writer. The solution is based on physically founded models of the respective imaging errors. With the proposed method, in contrast to known methods, it is possible to correct effectively mask structures designed for generating highly integrated circuits, although the calculational effort involved is significant. A further disadvantage of this method lies in the large number of parameters that must be taken into account in the form of correction values. Furthermore, in addition to diffraction and refraction effects, interactions and device-specific aberration effects must also be taken into account.

The unpublished German patent application DE 10 2007 028 260 describes a device for measuring positioning and structural widths or at least one structure on a surface of a substrate. The substrate is set into the measuring table in such a manner that a normal vector pointing out of the surface of the substrate which bears the structures is essentially parallel to the gravitational force vector.

None of the devices and/or methods known from the prior art is able to identify incorrect measurements so reliably that the throughput of the coordinate measuring machine is only insubstantially reduced, and to a degree that is acceptable to the user.

SUMMARY OF THE INVENTION

It is therefore an object of the present invention to provide a device which reliably identifies an incorrect measurement without the throughput of the coordinate measuring machine being unacceptably reduced thereby, and such that the short-term and long-term reproducibility and the accuracy of the measurement are optimised.

This aim is achieved with a device which comprises at least one reflected light illumination apparatus and/or a transmitted light illumination apparatus; at least one imaging optical system and one detector of a camera for imaging the structures on the substrate; a first program portion linked to the detector of the camera, wherein said detector is provided for determining the position and/or dimension of the structure on the substrate and wherein the device determines and records a plurality of measurement variables $M_j$, $j \in \{1, \ldots, L\}$, from which at least one variable G can be determined; a second program portion linked to the detector of the camera, wherein said program portion calculates an analysis of the measurement variables $M_j$ with regard to a possible incorrect measurement.

It is a further object of the invention to provide a method with which an incorrect measurement is reliably identified without the throughput of the coordinate measuring machine being unacceptably reduced thereby, and such that the short-term and long-term reproducibility and accuracy of the measurement are optimised.

The device according to the invention comprises at least one reflected light illumination apparatus and/or one transmitted light illumination apparatus with which the structures on a mask (substrate) are illuminated. In one embodiment, the at least one reflected light illumination apparatus and/or transmitted light illumination apparatus respectively emits light along a common optical axis. In a further embodiment, a measuring table which is displaceable perpendicularly and relative to the optical axis under interferometric control is provided for accommodating the mask and for positioning the structures on the mask. The displacement of the measuring table is therefore controlled and measured using interferometric means. The device also comprises at least one imaging optical system and a detector of a camera, so that the structures on the mask can be imaged on the detector of the camera by means of the at least one imaging optical system. In another embodiment, the camera is a CCD camera which is sensitive to light of a wavelength equal to or less than 400 nm. The device according to the invention also comprises a first program portion which is linked to the detector of the camera and is provided for determining the position and/or measurements of the structure on the mask. The device according to the invention therefore measures the structures on the mask using the previously described elements from the prior art.

During a measurement to determine the position and/or dimension of a single structure on the mask, incorrect measurements can occur due to internal and external influences on the device according to the invention. An incorrect measurement is taken to mean a measurement value that deviates from the mean value significantly more than could be expected due to the standard deviation. These measurement values are also known as spurious values, or "flyers" in the English literature. An incorrect measurement can be recognised by repeated measurement of the same structure and the relevant measurement values can be rejected (see FIG. 2). However, this is time-consuming and reduces the throughput of the device according to the invention. The idea of the underlying invention is therefore to recognise by suitable analysis of an individual measurement whether an incorrect measurement has been made or not. Only in the event of an incorrect measurement is a repeat measurement subsequently carried out. The throughput of the device according to the invention is thereby reduced only minimally and this would not normally be noticeable to the user.

In a complex device according to the present invention, during a measurement, a wide variety of measurement variables $M_j$, $j \in \{1, \ldots, L\}$, is detected and stored. The index j counts the individual measurement variables and L is the number of the measurement variables. These measurement variables $M_j$ may be, for example, temperature, pressure or intensity measurements. In the coordinate measuring machine of the applicant submitting the present patent application, the images of a CCD camera and interferometric measurements are also evaluated, and this therefore results in further measurement variables $M_j$. As a rule, the applicant is not concerned with the individual measurement variables $M_j$, but with a more complex variable G, for example the position or width of a structure on the mask. A variable G of this type can usually be calculated according to a prescribed function g from the at least one, or usually the plurality of, different measurement variables $M_j$:

$$G = g(M_1, \ldots, M_L) \qquad (1)$$

In one embodiment, the variable G is defined as the position of the structure on the mask. Several variables G can be determined.

In the device according to the invention, a second program portion is linked to the detector of the camera. The second program portion generates an analysis of the measurement variables $M_j$ with regard to a possible incorrect measurement using calculation rules given by the user. It is obvious to a person skilled in the art that the terms first program portion and second program portion do not represent limitations of the invention. How the individual program portions or subroutines are realised in the computer depends on the architecture used. What needs to be taken into account in the calculation rules for the second program portion will now be described in greater detail. The first and second program portion can be considered to be subroutines and, in accordance with normal programming techniques, can be called in a higher order program, or the first and second program portions may be considered to be components of a single program.

Since the individual measurement variables $M_j$ are each subject to their own statistical distribution, as is the case in every measuring process, on repeated measurement of the same structure, slight variations in the measurement variables $M_j$ occur. According to the rule function g, these variations also decline in size G. If the size G is calculated for each repeated measurement, then the mean value and the standard deviation can be calculated for G. The standard deviation is then a measure of the reproducibility of the measurement.

However, as a result of external influences on the measurement, such as vibration, pressure and temperature variations, etc., individual values of the variable G can lie further removed from the mean than would be expected due to the standard deviation. This can only be identified if the measurement is often repeated and the variable G is represented in a histogram (see FIG. 2).

In general, the user has little time in which to carry out these repeated measurements. In a normal case, therefore, he would only measure one particular mask several times, in order to determine the reproducibility of the device (coordinate measuring machine) once. When making later measurements, he would measure his sample only once and, in the event of a measuring error, assume the previously determined reproducibility. However, he could not be sure, in this later measurement, that an incorrect measurement which lies far outside the limits given by the reproducibility—i.e. standard deviation—has not occurred.

The purpose of the present invention is to decide, on the basis of the large number of measurement variables $M_j$, whether the actual respective measurement is an incorrect measurement of this type or not. In the event of an incorrect measurement being identified, the measurement is repeated. Since incorrect measurements are generally very rare, this procedure is not critical in terms of the time taken, and gives the user the certainty that his measuring error lies within the order of magnitude defined by the reproducibility—i.e. the standard deviation—of the device according to the invention.

In order to bring about the aforementioned decision, additional quality factors $Q_i = f_i(M_1, \ldots, M_L)$, $i \in \{1, \ldots, N\}$ are therefore determined from the plurality of measurement variables $M_j$. The index i counts the quality factors $Q_i$ and N is the number of quality factors $Q_i$. On repeat measurement, the quality factors $Q_i$ each have a characteristic distribution, each of which depends on the underlying measurement variables $M_j$ and the functions $f_i$. A quality factor $Q_i$ may be defined, for example, as a residual error function of a best fit curve to a series of measurement values. However, given a suitable choice of functions $f_i$, these distributions are independent of the respective actual measurement structure of the user and can also be determined when determining the reproducibility of the device according to the invention. A special case exists when $Q_i = M_j$ for $j \in \{1, \ldots, L\}$.

Figure 3:
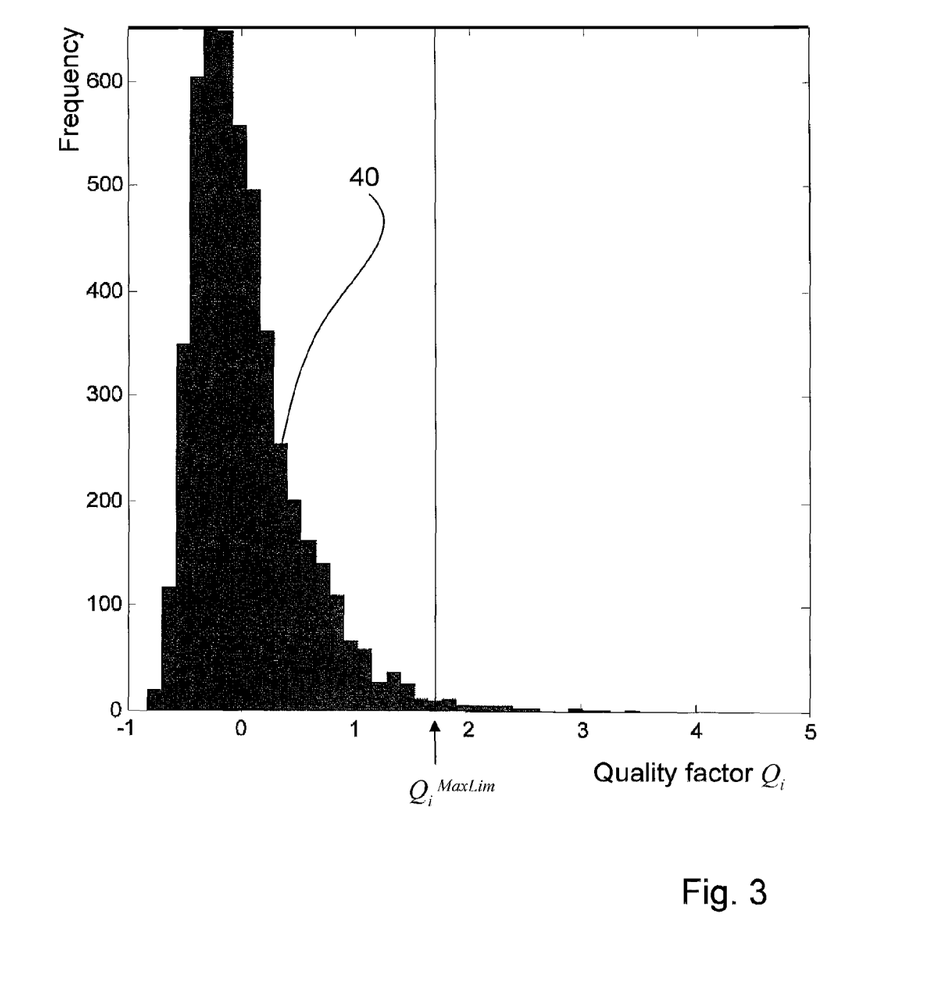
FIG. 3 shows a histogram with an upper limit $Q_i^{MaxLim}$ for the quality factor $Q_i$ at approximately 1.7, so that measurements which supply a value for $Q_i$ above 1.7 are rejected as a precaution.

Based on the distribution of the quality factors $Q_i$, limits $Q_i^{Lim}$ can be defined for the individual quality factors $Q_i$ (see FIG. 3). These may be upper limits (as in FIG. 3), lower limits (not shown) or range limits (not shown). If at least one quality factor $Q_i$ lies outside the permitted limits, the measurement is rejected as being an incorrect measurement and measuring is repeated. Using this technique, it is ensured that the device according to the invention is always in a well-defined condition. However, it is not precluded with the device or the method according to the invention that a good measurement is rejected. However, with suitable choice of the limits $Q_i^{Lim}$, the probability thereof is small, so that the throughput is not significantly influenced.

In a preferred embodiment of the present invention, the functions $f_i$ are determined so that the respective associated quality factor $Q_i$ correlates to the variable G. In this case, exceeding of the quality limit $Q_i^{Lim}$ by passing or undershooting (depending on the type of measurement variable $M_j$) also represents an incorrect measurement for this $Q_i$. The danger that a good measurement will be rejected is therefore significantly reduced.

In general, the various influences on the device according to the invention do not affect all the measurement variables $M_j$ equally. Thus, for example, a fault may influence only one single measurement variable $M_j$, whereas a second fault disrupts a whole set of measurement variables $M_j$. The attempt is therefore made to find a set of functions $f_i$ which have the following properties:

1. For every external influence i there is a function $f_i$.
2. The functions $f_i$ correlate to the variable G.

Under certain circumstances, particular situations cannot be read off with a single quality factor $Q_i$, but are revealed by a comparison of several quality factors $Q_i$ against one another. Herein, one or a plurality of global quality factors $Q_k^{Total}$, $k \in \{1, \ldots, O\}$ can be defined, wherein k is the running index and O is the number of global quality factors $Q_k^{Total}$:

$$Q_k^{Total} = h_k(Q_1, \ldots, Q_N) \quad (2)$$

Since the quality factors $Q_i$ are each a function of the measurement variables $M_j$, the global quality factors $Q_k^{Total}$ are also each a function of the measurement variables $M_j$:

$$Q_k^{Total} = h_k(M_1, \ldots, M_L) \quad (3)$$

The quality factors $Q_i$ have a precise meaning; for example, for an I, $Q_i$ can be the quality of the position of the measuring table. The function $h_k$ formed from the quality factors $Q_i$ is clearer in the interpretation than the interpretation of the function $h_k'$ from the measurement variables $M_j$. $Q_k^{Total}$ can be formed from $M_j$ or $Q_i$ according to the prior art.

In the embodiments of the present invention as described below, the upper and/or lower limits $Q_i^{Lim}$ for the quality factors $Q_i$ are defined, wherein the values of the quality factors $Q_i$ should lie below or above these limits in order that the associated measurement variables $M_j$ should not be rejected and no incorrect measurements arise. If, in one embodiment $Q_i^{Lim}$ is stipulated as the upper limit for $Q_i$, then an incorrect measurement has arisen if there is at least one determined $Q_i$ which undershoots this threshold $Q_i^{Lim}$: $\exists i : Q_i > Q_i^{Lim}$. If, instead of this, in another embodiment, $Q_i^{Lim}$ has been given a particular value as the lower limit, an incorrect measurement has taken place if there is at least one determined value $Q_i$ which undershoots this threshold $Q_i^{Lim}$: $\exists i : Q_i > Q_i^{Lim}$.

Additionally, in various other embodiments of the present invention, permitted or forbidden ranges are specified for the quality factors $Q_i$, wherein the values of the quality factors $Q_i$ should lie within or outside these ranges in order that the measurement values for the associated measurement variables $M_j$ should not be rejected and no incorrect measurement has occurred.

If, in one embodiment $[Q_i^{MinLim}; Q_i^{MaxLim}]$ is specified as the permitted range for $Q_i$, an incorrect measurement exists when there is at least one $Q_i$ which lies outside this interval, and $Q_i$ therefore either undershoots $Q_i^{MinLim}$ or exceeds $Q_i^{MaxLim}$: $\exists i : Q_i > Q_i^{MinLim} \vee Q_i > Q_i^{MaxLim}$. If, in another embodiment $[Q_i^{MinLim}; Q_i^{MaxLim}]$ is specified as the forbidden range for $Q_i$, then an incorrect measurement exists when there is at least one $Q_i$ which lies within this interval, that is $Q_i$ both exceeds $Q_i^{MinLim}$ and undershoots $Q_i^{MaxLim}$: $\exists i : Q_i^{MinLim} > Q_i > Q_i^{MaxLim}$.

In the embodiments described above, each respective $Q_i^{Lim}$ can also itself be a function of $Q_i : Q_i^{Lim} = Q_i^{Lim}(Q_1, \ldots, Q_N)$.

In one embodiment, when an incorrect measurement is detected, according to the above described procedures, a repeat measurement is automatically carried out. In a further embodiment, the repeat measurements are labelled, even though they do not represent incorrect measurements, to enable the user to analyse where problems have arisen.

However, it cannot be ruled out that a defective measuring structure in the device according to the invention outputs a signal which resembles an incorrect measurement. That means that there is at least one $Q_i$ which surpasses the permitted limit values $Q_i^{Lim}$ or limit ranges $[Q_i^{MinLim}; Q_i^{MaxLim}]$ or the global quality factors $Q_k^{Total}$ lie outside the permitted range or within the forbidden range. In this event, even where a measurement is repeated, it can be assumed that the quality factors $Q_i$ indicate an incorrect measurement. In order to prevent endless repetition of the measurement of this structure, in a preferred embodiment of the device according to the invention, an additional counter l is introduced which counts the number of repeat measurements, wherein a user inputs a maximum permitted number $l_{max}$ of repetitions, so that if $l_{max}$ is overshot, the last measurement is accepted and stored, but a marker is set by the second program portion to identify the measurement as uncertain. If, on later evaluation of the measurement data, anomalies should be found at this site in the data set or on the mask, then by means of this marking, it can be determined subsequently that there may have been a problem with this measurement.

In another embodiment, the device according to the invention comprises evaluation electronics which is linked to the detector of the camera and contains the first program portion and the second program portion.

In accordance with the above described device, the invention also provides a method for automatic detection of a possible incorrect measurement and this will be described now. The features of the method corresponding to those of the device according to the invention will only be mentioned briefly, whilst the other steps of the method will be described in detail.

In the method according to the invention, at least one structure is illuminated on the mask (substrate) for semiconductor production using at least one reflected light illumination apparatus and/or one transmitted light illumination apparatus. As described above, in one embodiment, the at least one reflected light illumination apparatus and/or the transmitted light illumination apparatus can emit light along a common optical axis or, in another embodiment, a measuring table for receiving the mask and for travelling toward the structures on the mask which is displaceable perpendicularly and relative to the optical axis under interferometric control can be provided. Furthermore, using at least one imaging optical system, the respectively selected structure on the mask is imaged on a detector of a camera. As described above, in one embodiment, the camera can be a CCD camera sensitive to light of a wavelength less than or equal to 400 nm.

Furthermore, for measuring the respective selected structure on the mask in relation to the position and/or dimension, the values are determined with a first utility program which is linked to the detector of the camera and a plurality of measurement variables $M_j$, $j\in\{1,\ldots,L\}$ is detected and recorded, from which at least one variable G is determined. The variable G is defined as the position of the structure on the substrate or as CD (Critical Dimension). Thereafter, an analysis of the measurement variables $M_j$ is calculated using a second program portion with regard to a possible incorrect measurement, said program portion being linked to the detector of the camera. As described above, in the method according to the invention, evaluating electronics linked to the detector of the camera and comprising the first program portion and the second program portion can be provided, wherein the first and second program portions can be regarded as being subroutines and can be called in a higher order program or higher order programs, or alternatively comprise part of a program.

Determination of whether an incorrect measurement has occurred is carried out as described above using the stated measurement variables, (global) quality factors, functions, limits and permitted or forbidden ranges.

Furthermore, in a preferred embodiment of the method according to the invention, in the event that an incorrect measurement is detected, a repeat measurement can be carried out automatically. In further embodiments of the method, a counter can be provided which counts the number of repeat measurements, wherein a user defines a maximum permissible number of repeats, so that if this number is exceeded, the last measurement is accepted. In addition, the measurement which was accepted on the basis of exceeding the maximum permissible number of repeats can be specially identified with a marking so that it is clear to the user that the maximum permissible number of incorrect measurements was exceeded. Furthermore, a plurality of limits $Q_i^{Lim}$, $Q_i^{MinLim}$, $Q_i^{MaxLim}$ can be determined from one measurement. This is carried out in an extra-calibration measurement.

The limits can be obtained from a repeated measurement of a mask and the $Q_i$ can be entered in a histogram and the limits can be set such that a particular percentage of the $Q_i$ to be specified by the user lies within or above or below or outside the limits. The limits can be specified by the user such that they lie a multiple of the standard deviation of the $Q_i$ around the mean value.

BRIEF DESCRIPTION OF THE DRAWINGS

The device according to the invention and the method according to the invention will now be described in greater detail making use of the schematic drawings, in which.

DETAILED DESCRIPTION OF THE PREFERRED EMBODIMENTS

Figure 1:
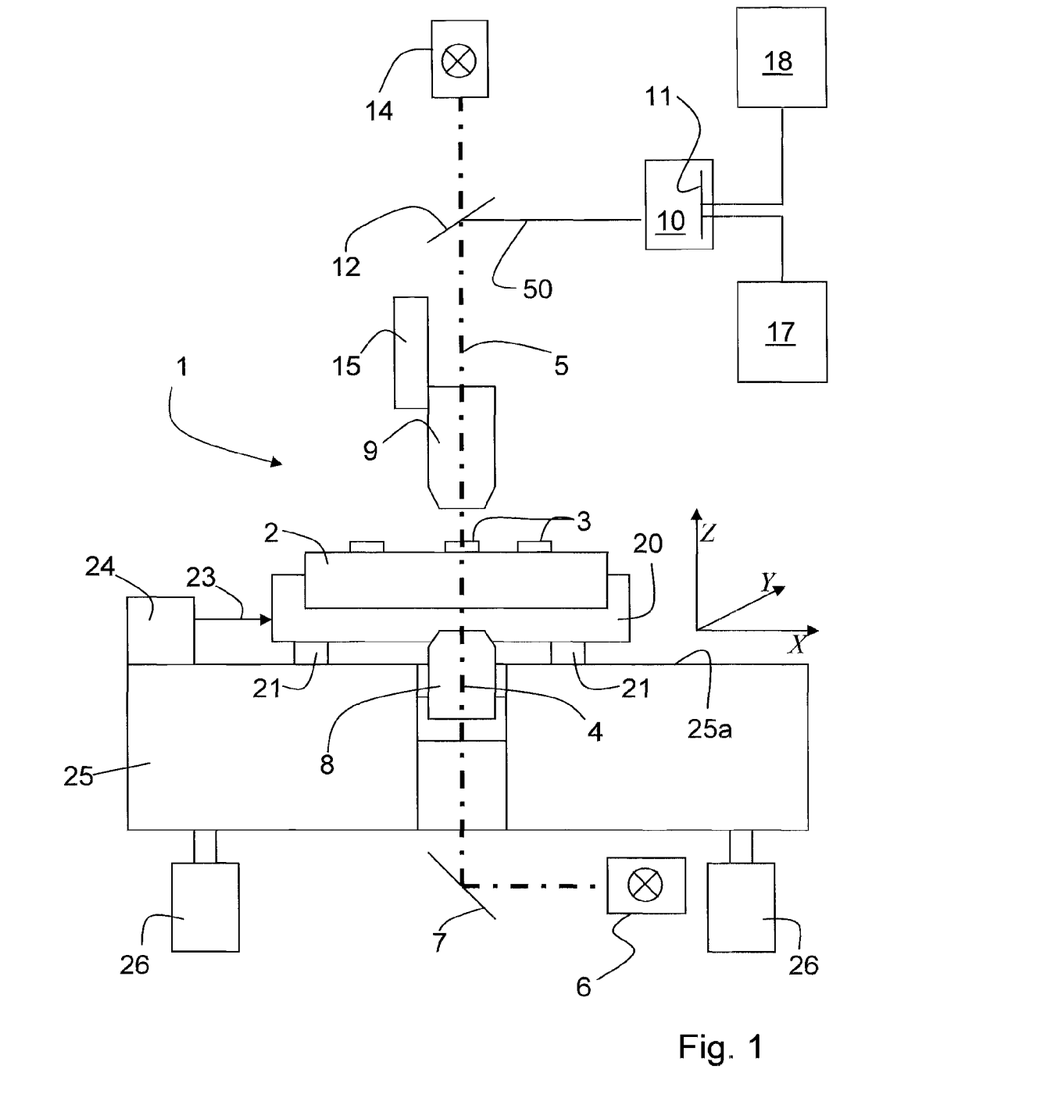
FIG. 1 shows a schematic representation of an embodiment of a device for measuring the positions of structures on a substrate.

FIG. 1 shows a schematic representation of an embodiment of a coordinate measuring machine 1 as previously described in detail in the prior art and therefore also known in detail from the prior art. The coordinate measuring machine 1 comprises a measuring table 20 movable in the X-coordinate direction and in the Y-coordinate direction. The measuring table 20 carries a substrate 2 which may be a mask 2 made, for example, from quartz glass. The mask 2 is used for the production of semiconductors, for example, wafers. A plurality of structures 3 is placed on the surface of the substrate 2. The measuring table 20 itself is supported on guide bearings or air bearings 21 which in turn can be supported on a granite block 25. Other types of block are also conceivable. It is herein only required that the block defines a plane 25a in which the measuring table 20 can be displaced. For the illumination of the substrate 2, at least one reflected light illumination apparatus 14 and/or one transmitted light illumination apparatus 6 is provided. In the embodiment illustrated here, the light from the transmitted light illumination apparatus 6 is reflected by means of a deflecting mirror 7 into the lower illumination axis 4 for the transmitted light. The light from the transmitted light illumination apparatus 6 exceeds via a condenser 8 to the substrate 2. The light from the reflected light illumination apparatus 14 passes via the imaging optical system 9 to the substrate 2. The light emerging from the substrate 2 is collected by the imaging optical system 9 and is reflected out of the optical axis comprising the illumination axes 4, 5 by a semi-silvered mirror 12. This measuring light arrives at a camera 10 provided with a detector 11. A first program portion 17 with which digital images can be generated from the recorded data and evaluated is assigned to the detector 11. In the embodiment according to FIG. 1, the detector 11 of the camera 10 is also linked to a second program portion 18 which calculates an analysis of the measurement variables $M_j$ with regard to a possible incorrect measurement.

The position of the measuring table 20 is measured by means of a laser interferometer 24 and determined. The displacement of the measuring table 20 is therefore monitored and measured by interferometric means. For this purpose, the laser interferometer 24 emits a measuring light beam 23. The imaging optical system 9 is also linked to a displacing device 15 in the Z-coordinate direction, so that the imaging optical system 9 can be focused on the surface of the substrate 2. The position of the imaging optical system 9 may be measured, for example, with a glass scale (not shown). The granite block 25 is also placed on feet 26 mounted in vibration damping manner. This vibration damping is intended to reduce or eliminate all possible building vibrations and intrinsic vibrations of the coordinate measuring machine 1 to the greatest possible extent. It is self-evident that the granite block 25 does not represent a limitation of the invention. Any block-like structure that is suitable for providing a plane 25a in which the measuring table 20 can be displaced can be used.

Figure 2:
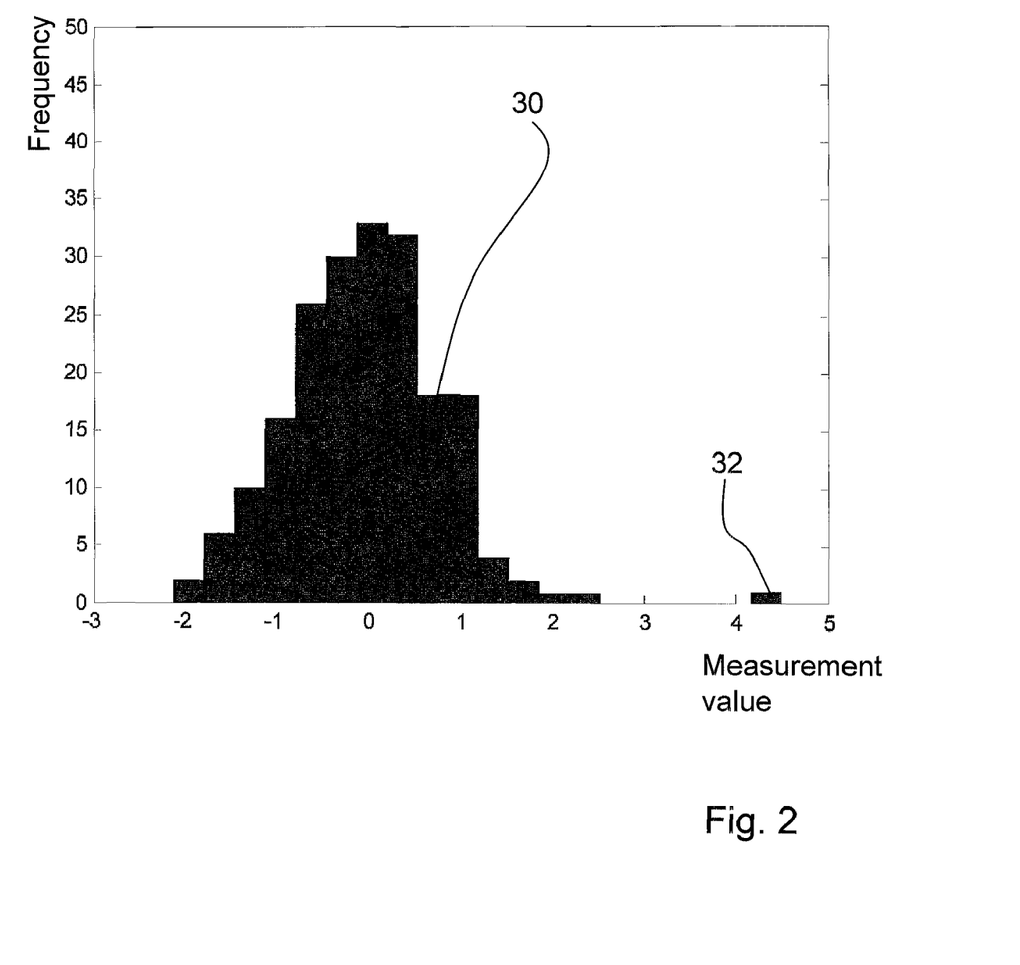
FIG. 2 shows a histogram with an incorrect measurement which can be identified by repeated measuring of the same structure on the mask and wherein the relevant values for the corresponding measurement variable $M_j$ are rejected.

FIG. 2 shows a histogram 30 with an incorrect measurement 32 which can be identified by repeated measurement of the same structure 3 on the mask (substrate 2). The histogram 30 shows the frequencies of the measurement values for a selected measurement variable $M_j$ for a selected. The mean value of the measurement values for the measurement variable $M_j$ lies at the measurement value 0. Also, among the measurements of $M_j$ on which FIG. 2 is based, few measurement values in the range between 4 and 5 were found that lay far outside the great majority of measurement values around the mean value and which lie with certainty outside the region of the mean value with the standard deviation, so that these relevant values relating to the relevant measurement variable $M_j$ would be rejected and classified as incorrect measurements. For this purpose, according to the present invention, previously relevant quality factors $Q_i$ with a suitable upper limit $Q_i^{MaxLim}$ and/or a suitable permitted range $[Q_i^{MinLim}; Q_i^{MaxLim}]$ are set. For each $j \in \{1, \ldots, L\}$, an appropriate histogram 30 can be created for the relevant measurement variable $M_j$.

FIG. 3 shows a histogram 40, wherein for a selected i, the frequencies of the values determined for the relevant quality factor $Q_i$ are plotted. The mean value of the quality factor $Q_i$ is zero. The standard deviation is significantly smaller than 1.7. Setting an upper limit $Q_i^{MaxLim}$ for the quality factor $Q_i$ at approximately 1.7 so that all the measurements that supply a value for $Q_i$ above 1.7 are rejected as a precaution suggests itself. For every $i \in \{1, \ldots, N\}$, a corresponding histogram 40 can be plotted at the relevant quality factor $Q_i$.

Figure 4:
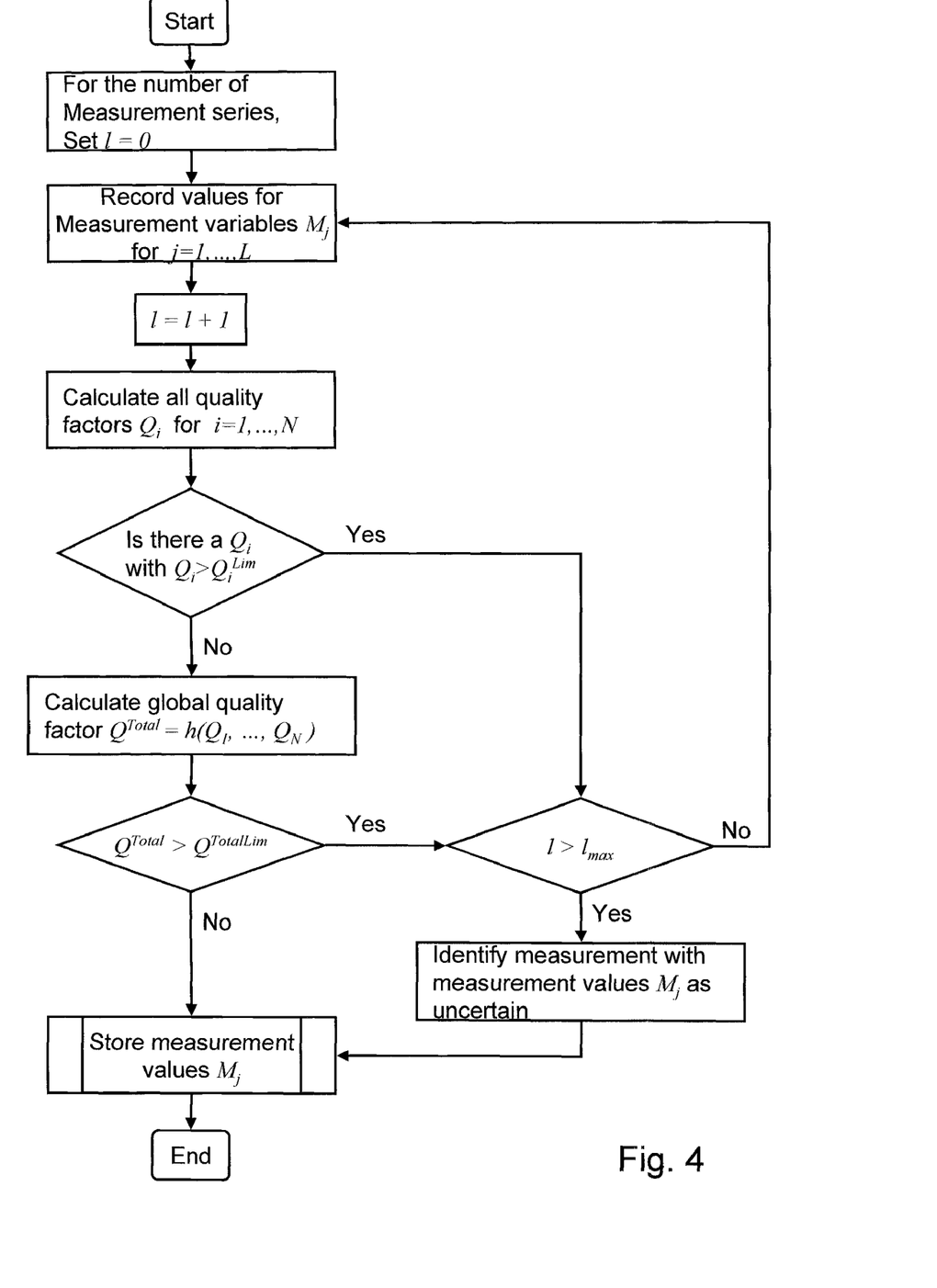
FIG. 4 shows a flow diagram for one embodiment of the method according to the invention.

FIG. 4 shows a flow diagram of one embodiment of the method according to the invention, having a single global quality factor $Q^{Total}$, that is, $O=1$. The $Q_i^{Lim}$ values represent upper limits for $Q_i$. In this embodiment, a measurement is rejected either if it yields an i with $Q_i > Q_i^{Lim}$ or if $Q^{Total} > Q^{TotalLim}$.

Before the measurement series is carried out, the maximum permissible number $l_{max}$ of repeats of measurements, the limits $Q^{Lim}$ for the quality factors $Q_i$ and the limit $Q^{TotalLim}$ for the global quality factor $Q^{Total}$ are predetermined by the user—as a rule, once for all measurement series—(in the embodiment according to FIG. 4, $O=1$).

Before the start of a measurement series, the counter I for the previously performed measurements is initialised with the value 0. For each respective counter value I, for $j=1, \ldots, L$, the measurement values $M_j$ are recorded. Also for each counter value I, the quality factors $Q_i$ are calculated for all $i=1, \ldots, N$. In the embodiment according to FIG. 4, the limits for the quality factors $Q_i$ are the upper limits $Q_i^{Lim}$. It is now tested whether at least one of the calculated values of $Q_i$ lies above its associated limit $Q_i^{Lim}$.

If all values of $Q_i$ are smaller than or equal to $Q_i^{Lim}$, this is not sufficient to be able to decide that no incorrect measurement has been made. In this event, the global quality factor $Q^{Total}$ is also calculated from the $Q_i$ values by means of the function h and it is then checked whether for these measurements, for the respective counter value l, $Q^{Total}$ is also larger than $Q^{TotalLim}$. If $Q^{Total}$ is smaller than or equal to $Q^{TotalLim}$, no incorrect measurement has been made, the measurement values for the Mj for the respective l are stored and no further measurements need to be carried out (i.e. the counter l is stopped). The method is thereby ended.

If all values of $Q_i$ are smaller than or equal to $Q_i^{Lim}$, $Q^{Total}$ is nevertheless greater than $Q^{TotalLim}$, and next a check must be made as to whether the counter I exceeds the maximum permissible number $l_{max}$ of repetitions of measurements, and if so, then all measurements of Mj for the respective I are identified as uncertain and stored, and the method is ended; if not, the measurements and tests for the $M_j$ are repeated for the next I as described above in relation to FIG. 4.

If, for the respective counter value I, at least one $Q_i$ is greater than $Q_i^{Lim}$, then no global quality factor $Q^{Total}$ is calculated, but rather a check is immediately made as to whether the counter l exceeds the maximum permissible number $l_{max}$ of repetitions of measurements; if so, then all the measurements for which Mj is identified as uncertain for the respective I are stored and the method is ended; if not, then the measurements and tests for the Mj are repeated for the next I, as described above in relation to FIG. 4.

Figure 5:
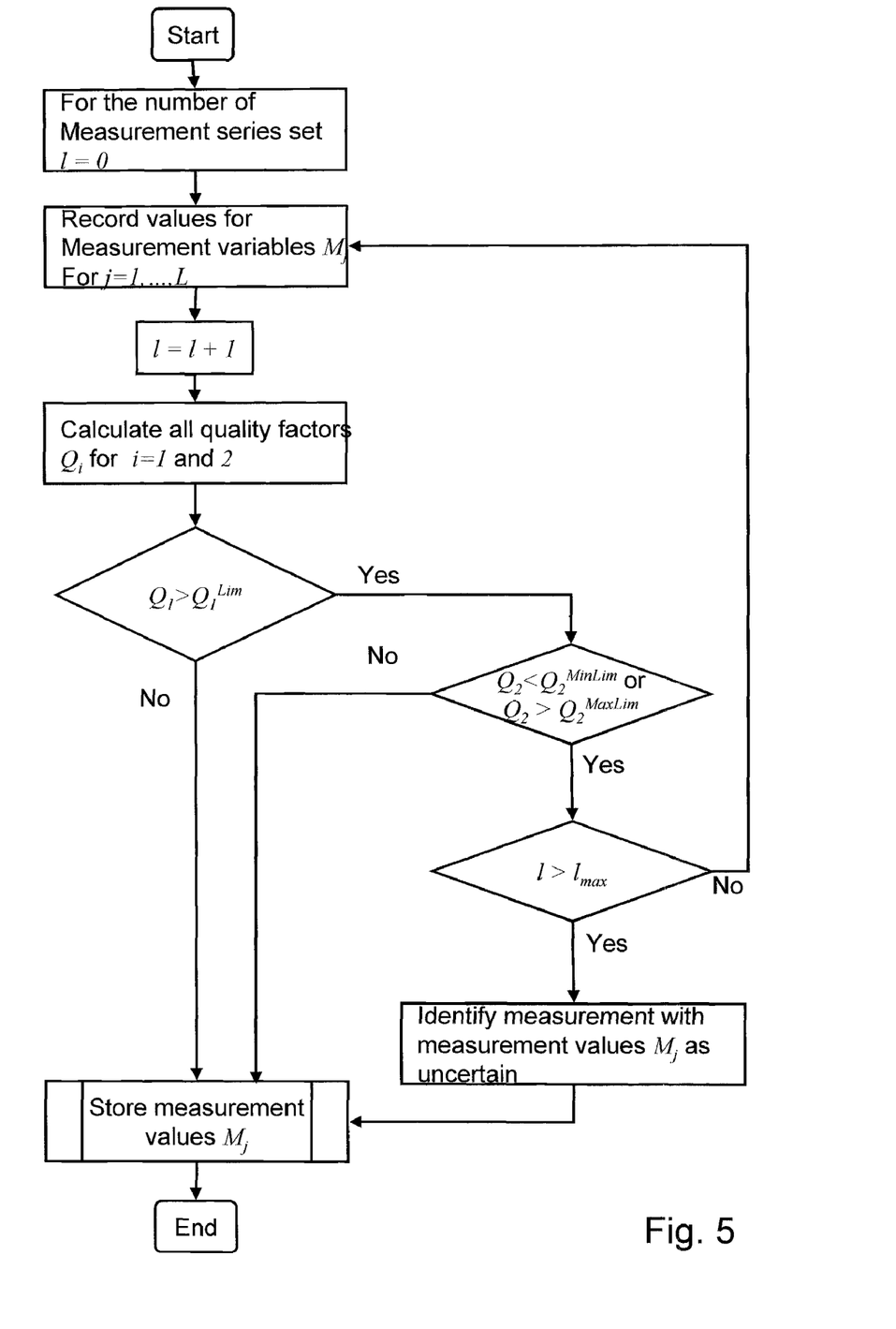
FIG. 5 shows a flow diagram for a further embodiment of the method according to the invention with a query for each of two conditions.

FIG. 5 shows a flow diagram of a further embodiment of the method according to the invention with one query to each of two conditions.

As described above, it is useful in some situations to exclude certain ranges in the N-dimensional space of $Q_i$ by specifying certain limits or intervals for $Q_i$. This is shown in FIG. 5 for a two-dimensional case (N=2).

Before the measurement series are carried out by the user, and as in FIG. 4, the maximum permissible number $l_{max}$ of repetitions of measurements and the upper limit $Q_1^{Lim}$ for the quality factor $Q_1$, and the lower limit $Q_2^{Lim}$ for the quality factors $Q_1$, $Q_2$ are first specified by the user. However, in contrast to FIG. 4, in the embodiment according to FIG. 5, no global quality factors $Q_k^{Total}$ are calculated and therefore also no limits $Q_k^{TotalLim}$ are specified.

As in FIG. 4, before a measurement series is begun, the counter I for the previously performed measurements is initialised to the value 0. Then for each counter value I, the measurement values are determined for all the measurement variables $M_j$ for all $j=1, \ldots, L$ and assigned the respective counter value l. Also for each counter value I, all the quality factors are calculated; in the embodiment according to FIG. 5, only $Q_1$ and $Q_2$ are calculated.

It is now checked whether $Q_1$ lies above its associated upper limit $Q_1^{Lim}$; if not, then $Q_2$ no longer need be observed, since in the embodiment according to FIG. 5, it is concluded therefrom that in every case $Q_2$ lies within its permitted range $[Q_2^{MinLim}; Q_2^{MaxLim}]$, the measurement values for $M_j$ are stored for each respective I and no further measurements need to be carried out (i.e. the counter l is stopped). The method is thereby ended.

If, however, $Q_1$ is greater than $Q_1^{Lim}$, then it is also checked whether $Q_2$ lies outside its permitted range $[Q_2^{MinLim}; Q_2^{MaxLim}]$;

If $Q_1$ is greater than $Q_1^{Lim}$ and $Q_2$ lies within the permitted range $[Q_2^{MinLim}; Q_2^{MaxLim}]$, the measurement values for the Mj for the respective l are stored and no further measurements need to be carried out (i.e. the counter l is stopped). The method is thereby ended.

If $Q_1$ is greater than $Q_1^{Lim}$ and $Q_2$ lies outside the permitted range $[Q_2^{MinLim}; Q_2^{MaxLim}]$, it must next be checked whether the counter l exceeds the maximum permissible number $l_{max}$ of repetitions of measurements; if so, all measurements for which Mj is identified for the respective l as uncertain, are stored and the method is ended; if not, the measurements and checks for the Mj are repeated for the next l.

In general, the testing principle just described can be extended to N>2 and can include as many $Q_i$ as desired. In this case, the limits $Q_i^{Lim}$ are therefore themselves functions of $Q_i$.

The embodiments according to FIGS. 4 and 5 can naturally be combined with each other. It can also not be stated by way of restriction that upper limits are used in the embodiments according to FIGS. 4 and 5. Rather, lower limits and permitted or forbidden ranges are also conceivable.

By way of conclusion, it should be stated quite specifically that the invention has been described making reference to preferred exemplary embodiments. However, it is obvious to a person skilled in the art that derivations and amendments can be undertaken without thereby departing from the protective scope of the following claims. In particular, the device according to the invention is not restricted to the specified embodiments for measurement variables and quality factors, but other embodiments are also conceivable without departing from the protective scope of the invention.

What is claimed is:

1. A device for automatic detection of a possible incorrect measurement during the determination of the position and/or dimension of a structure on a substrate, the device comprises:
   at least one reflected light illumination apparatus and/or a transmitted light illumination apparatus;
   at least one imaging optical system and one detector of a camera for imaging the structures on the substrate;
   a first program portion linked to the detector of the camera, wherein said detector is provided for determining the position and/or dimension of the structure on the substrate and wherein the device determines and records a plurality of measurement variables $M_j$, j belonging to the group of $\{1, \ldots, L\}$, from which at least one variable G can be determined; and
   a second program portion linked to the detector of the camera,
   wherein said second program portion calculates an analysis of the measurement variables $M_j$ with regard to a possible incorrect measurement,
   wherein the possible incorrect measurement is determined by examining a plurality of quality factors $Q_i$, i belonging to the groups of $\{1, \ldots, N\}$, wherein the quality factors $Q_i$ can be determined from the measurement variables $M_j$, wherein each quality factor $Q_i$ is determined according to a rule fi from the measurement variables $M_j$: $Q_i = f_i(M_1, \ldots, M_L)$, and
   wherein the rule $f_i$ is selected such that the associated quality factor $Q_i$ correlates to the variable G.

2. The device according to claim 1, wherein the at least one reflected light illumination apparatus and/or transmitted light illumination apparatus each emit light along a common optical axis.

3. The device according to claim 1, wherein the device comprises a measuring stage, which is displaceable under interferometric control perpendicularly and relative to an optical axis, for accommodating the substrate and for positioning the structures on the substrate in the optical axis.

4. The device according to claim 1, wherein an evaluating electronic is linked to the detector of the camera comprises the first program portion and the second program portion.

5. The device according to claim 1, wherein the camera is a CCD camera, that is sensitive to light of a wavelength less than or equal to 400 nm.

6. A method for automatic detection of a possible incorrect measurement during the determination of the position or dimension of a structure on a substrate, the device comprises the following steps:
   illuminating at least one of the structures on the substrate for semiconductor production with at least one reflected light illumination apparatus and/or a transmitted light illumination apparatus;
   imaging the structure on the substrate on a detector of a camera with at least one imaging optical system;
   determining during measurement of the structure on the substrate in relation to the position and/or dimension the values with a first program portion which is linked to the detector of the camera;
   detecting and recording a plurality of measurement variables $M_j$, j belonging to the group of $\{1, \ldots, L\}$, from which at least one variable G is determined; and
   calculating an analysis of the measurement variables $M_j$ with regard to a possible incorrect measurement with a second program portion which is linked to the detector of the camera,
   wherein the possible incorrect measurement is determined by examining a plurality of quality factors $Q_i$, i belonging to the groups of $\{1, \ldots, N\}$, wherein the quality factors $Q_i$ can be determined from the measurement variables $M_j$, wherein each quality factor $Q_i$ is determined according to a rule fi from the measurement variables $M_j$: $Q_i = f_i(M_1, \ldots, M_L)$, and
   wherein the rule $f_i$ is chosen such that the associated quality factor $Q_i$ correlates to the position measurement of the structure on the substrate.

7. The method according to claim 6, wherein the possible incorrect measurement is identified when at least one $Q_i$ exceeds a threshold $Q_i^{Lim}$, wherein $\exists i: Q_i > Q_i^{Lim}$ applies.

8. The method according to claim 6, wherein the possible incorrect measurement is identified when at least one $Q_i$ undershoots a threshold $Q_i^{Lim}$, wherein $\exists i: Q_i < Q_i^{Lim}$ applies.

9. The method according to claim 6, wherein the possible incorrect measurement is identified when at least one $Q_i$ lies outside a permitted range, wherein $\exists i: Q_i < Q_i^{Lim} \vee Q_i > Q_i^{MaxLim}$ applies.

10. The method according to claim 6, wherein the possible incorrect measurement is identified that at least one $Q_i$ lies within a forbidden region, wherein $\exists i: Q_i^{MinLim} \vee Q_i > Q_i^{MaxLim}$ applies.

11. The method according to claim 6, wherein the possible incorrect measurement is identified when at least one $Q_i$ exceeds a threshold $Q_i^{Lim}$ and $Q_i^{Lim}$ is itself a function of the $Q_i: \exists i: Q_i > Q_i^{Lim}$; wherein $Q_i$ are $Q_1, \ldots, Q_N$.

12. The method according to claim 6, wherein the possible incorrect measurement is identified when at least one $Q_i$ undershoots a threshold $Q_i^{Lim}$ and $Q_i^{Lim}$ is itself a function of the $Q_i: \exists i: Q_i < Q_i^{Lim}$; wherein $Q_i$ are $Q_1, \ldots, Q_N$.

13. The method according to claim 6, wherein the possible incorrect measurement is identified when at least one $Q_i$ lies within a forbidden region and $Q_i^{LimMin}$ and $Q_i^{LimMax}$ are themselves a function of the $Q_i: \exists i: Q_i^{MinLim} < Q_i < Q_i^{MaxLim}$; wherein $Q_i$ are $Q_1, \ldots, Q_N$.

14. Method according to claim 6, wherein the possible incorrect measurement is identified when at least one $Q_i$ lies outside a permitted range and $Q_i^{LimMin}$ and $Q_i^{LimMax}$ are themselves a function of the $Q_i: \exists i: Q_i < Q_i^{MinLim} \vee Q_i > Q_i^{MaxLim}$; wherein $Q_i$ are $Q_1, \ldots, Q_N$.

15. The method according to claim 6, wherein if an incorrect measurement is detected, a repeat measurement is automatically carried out.

16. The method according to claim 15, wherein repeat measurements are identified independently of whether they represent incorrect measurements or not.

17. The method according to claim 16, wherein a counter is provided which counts the number of repeat measurements, wherein a user specifies a maximum permissible number of repeats, so that on exceeding this number, the last measurement is accepted.

18. A method for automatic detection of a possible incorrect measurement during the determination of the position or dimension of a structure on a substrate, comprises the following steps:
   illuminating at least one of the structures on the substrate for semiconductor production with at least one reflected light illumination apparatus and/or a transmitted light illumination apparatus;
   imaging the structure on the substrate on a detector of a camera with at least one imaging optical system;
   determining during measurement of the structure on the substrate in relation to the position and/or dimension the values with a first program portion which is linked to the detector of the camera;

detecting din a plurality of measurement variables $M_j, j \in \{1, \ldots, L\}$, from which at least one variable G is determined; and calculating an analysis of the measurement variables $M_j$ with regard to a possible incorrect measurement with a second program portion which is linked to the detector of the camera;

wherein the possible incorrect measurement is determined by means of a plurality of quality factors $Q_i$, wherein the quality factors $Q_i$ can be determined from the measurement variables $M_j$ wherein each quality factor $Q_i$ is determined according to a rule $f_i$ from the measurement variables $M_j$: with $Q_i = f_i(M_1, \ldots, M_L)$;

wherein if an incorrect measurement is detected, a repeat measurement is automatically carried out;

wherein repeat measurements are identified independently of whether they represent incorrect measurements or not;

wherein a counter is provided which counts the number of repeat measurements, wherein a user specifies a maximum permissible number of repeats, so that on exceeding this number, the last measurement is accepted; and wherein the accepted measurement, which was accepted on the basis of the exceeding of the maximum permissible number of repeats, is specifically identified with a marking in order to make it clear to the user that the maximum number of incorrect measurements has been exceeded.

19. A method for automatic detection of a possible incorrect measurement during the determination of the position or dimension of a structure on a substrate, comprises the following steps:

illuminating at least one of the structures on the substrate for semiconductor production with at least one reflected light illumination apparatus and/or a transmitted light illumination apparatus;

imaging the structure on the substrate on a detector of a camera with at least one imaging optical system;

determining during measurement of the structure on the substrate in relation to the position and/or dimension the values with a first program portion which is linked to the detector of the camera;

detecting and recording a plurality of measurement variables $M_j, j \in \{1, \ldots, L\}$, from which at least one variable G is determined; and calculating an analysis of the measurement variables $M_j$ with regard to a possible incorrect measurement with a second program portion which is linked to the detector of the camera;

wherein the possible incorrect measurement is determined by means of a plurality of quality factors $Q_i$, wherein the quality factors $Q_i$ can be determined from the measurement variables $M_j$ wherein each quality factor $Q_i$ is determined according to a rule $f_i$ from the measurement variables $M_j$: with $Q_i = f_i(M_1, \ldots, M_L)$; and wherein a plurality of limits $Q_i^{Lim}$, $Q_i^{MinLim}$, $Q_i^{MaxLim}$ is determined from one calibration measurement.

20. The method according to claim 19, wherein the limits are obtained from a repeated measurement of a substrate and the $Q_i$ values are plotted in a histogram such that a particular percentage of the $Q_i$ values to be set by a user lies within or above or below or outside the limits.

21. The method according to claim 20, wherein the limits lie at a multiple—to be set by the user—of the standard deviation of the $Q_i$ values.

* * * * *

UNITED STATES PATENT AND TRADEMARK OFFICE
CERTIFICATE OF CORRECTION

PATENT NO. : 8,154,595 B2
APPLICATION NO. : 12/023222
DATED : April 10, 2012
INVENTOR(S) : Hans-Artur Boesser et al.

It is certified that error appears in the above-identified patent and that said Letters Patent is hereby corrected as shown below:

In Claim 6, column 13, line 47, after the word "substrate," delete the words "the device", In Claim 6, column 14, line 1, replace "groups" by "group", In Claim 6, column 14, line 5, replace "$M_l$" by "$M_L$", In Claim 18, column 15, line 1, replace "din" by "and recording".

Signed and Sealed this
Twenty-fourth Day of July, 2012

David J. Kappos
*Director of the United States Patent and Trademark Office*